United States Patent
Schultz et al.

(10) Patent No.: US 6,231,651 B1
(45) Date of Patent: May 15, 2001

(54) ENHANCED WOOD PRESERVATIVE COMPOSITION

(75) Inventors: Tor P. Schultz; Darrel D. Nicholas, both of Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 09/336,334

(22) Filed: Jun. 18, 1999

(51) Int. Cl.[7] .......................... A01N 25/22; A01N 31/08; A01N 43/653; A01N 31/02; A01N 33/00
(52) U.S. Cl. .................. 106/18.32; 252/401; 252/403; 252/404; 514/383; 514/456; 514/646; 514/667; 514/731
(58) Field of Search .............. 106/18.32; 252/401, 252/403, 404; 514/383, 456, 646, 667, 731

(56) References Cited

U.S. PATENT DOCUMENTS

| | | | |
|---|---|---|---|
| 1,168,062 | 1/1916 | Deppeler | 156/227 |
| 3,881,940 | 5/1975 | Amundsen et al. | 106/15 |
| 3,889,020 | 6/1975 | Amundsen et al. | 427/297 |
| 4,400,298 | 8/1983 | Boocock et al. | 252/400 |
| 4,761,247 * | 8/1988 | Rei et al. | 252/364 |
| 4,783,221 | 11/1988 | Grove | 106/18.22 |
| 4,839,373 | 6/1989 | Ito et al. | 514/367 |
| 4,950,685 | 8/1990 | Ward | 514/479 |
| 4,977,186 | 12/1990 | Gruening | 514/479 |
| 5,179,116 | 1/1993 | Goettsche et al. | 514/388 |
| 5,185,214 | 2/1993 | LeVan et al. | 428/541 |
| 5,300,520 | 4/1994 | Igarashi et al. | 514/367 |
| 5,462,589 | 10/1995 | Nicholas et al. | 106/18.33 |
| 5,536,305 | 7/1996 | Yu | 106/18.33 |
| 5,540,954 * | 7/1996 | Nicholas et al. | 427/397 |
| 5,634,967 | 6/1997 | Williams et al. | 106/18.32 |
| 5,730,907 | 3/1998 | Schultz et al. | 252/400.62 |
| 5,944,880 * | 8/1999 | Schultz et al. | 106/18.33 |

FOREIGN PATENT DOCUMENTS

| | | |
|---|---|---|
| 2 025 469 | 1/1980 | (GB). |
| 97.45236 * | 4/1997 | (WO). |

OTHER PUBLICATIONS

Imsgard, F., et al., B.W.P.A. Annual Convention, pp. 47–54, Jun. 1985.

Schultz, T., et al., Phytochemistry, vol. 29, No. 5. pp. 1501–1507, 1990, No Month.

Nicholas, D.D., Proc. of the Northern Hardwood Resource: Management and Potential Conference, Houghton, MI, Aug. 18–20(Aug. 1986).

Preston, A. F., et al., Proc. Am. Wood Preservers' Assn., 79, 207(Apr. 1983).

* cited by examiner

*Primary Examiner*—Anthony Green
(74) *Attorney, Agent, or Firm*—Darby & Darby

(57) ABSTRACT

A wood preservative composition comprising at least one biocide, such as an iodopropargyl compound or a triazole compound, in combination with at least one antioxidant, such as a hindered phenol, a flavonoid compound, or a naturally occurring polyphenol derived from a woody plant, is useful as a cost-effective and environmentally safe wood preservative. The invention also provides a method for the use of such composition and compositions so treated.

33 Claims, No Drawings

ENHANCED WOOD PRESERVATIVE COMPOSITION

BACKGROUND OF THE INVENTION

Hardwoods constitute over one-third of the U.S. timber resource. However, with the exception of cross-ties, hardwoods are rarely treated for exterior use applications, and demand for treated hardwood products has until recently been low. In view of the projected softwood timber shortage and relative abundance of hardwoods, expanded use of treated hardwoods for both composite and solid wood products is expected. The problem is that replacing softwoods with hardwoods is not straightforward since most wood preservatives, including second generation biocides, are considerably less effective when used to treat hardwoods. (Nicholas, D. D., Proc. of the Northern Hardwood Resource: Management and Potential Conference, Houghton, Mich., Aug. 18–20 (1986); Preston, A. F., et al., Proc. Am. Wood Preservers' Assn., 79, 207 (1983)). This disparity is attributable to the considerably higher toxic threshold values obtained when treated hardwoods are attacked by white- and soft-rot fungi as compared to softwoods treated with the same biocide and exposed to brown-rot fungi. (Nicholas, supra.) Accordingly, the object of the present invention is to provide wood preservative systems that are effective in protecting hardwoods and providing greater efficacy for softwoods.

An apparent solution to the problem of preserving hardwoods is to use substantially higher biocide levels, but this approach leads to higher costs and increased environmental risks. A more attractive solution would be to increase the efficacy of biocides for treating hardwoods.

In addition, more environmentally benign preservatives to treat softwoods are needed, since all major wood preservatives used today to protect softwoods have perceived environmental problems.

DESCRIPTION OF RELATED ART

Prior to the present invention, antioxidants have been used in wood treatments of various kinds to stabilize the mixture from chemical decomposition or as a color stabilizer. For example, U.S. Pat. No. 1,168,062 discloses the use of oxidation inhibitors as an additive in oil-in-water emulsions for use in wood preservatives which contain pentachlorophenol as the active ingredient. U.S. Pat. No. 3,889,020 provides di-tert-butyl cresol (also called butylated hydroxytoluene, or BHT) as a stabilizer for pentachlorophenol-based preservatives wherein the cresol is intended to improve the surface color of treated poles.

U.K. Patent Application GB 2,025,769A discloses the use of antioxidants, selected from such compound classes as sulfites, hydrosulfides, hydrazines and thiosemicarbazides. The purpose of the antioxidant there is to stabilize biocides from decomposition. U.S. Pat. No. 3,881,940 describes a composition containing an antioxidant stabilizer such as di-tert-butylcresol in a biocide comprising a heavy metal oxide and pentachlorophenol. The antioxidant served to prevent discoloration of wood and to prevent sludge formation during treating steps. U.S. Pat. No. 4,400,298 teaches the combination of dithiocarbamate and a borate with an antioxidant stabilizing agent, e.g., potassium metabisulfite, for the prevention of fungal decay in wood. U.S. Pat. No. 4,783,221 describes wood preservatives containing an isothiazolone and metal salts of carboxylic acids, to which various additives are added including antioxidants. U.S. Pat. No. 5,462,589 discloses a synergistic wood preservative composition comprising copper and organic derivatives, of which antioxidants are recited as possible additives.

Various biocides have also been used to preserve wood. U.S. Pat. No. 4,977,186 teaches a composition for preserving wood comprising iodopropargyl biocides with a pyrethroid-type insecticide. U.S. Pat. No. 5,634,967 teaches a composition for preserving wood comprising a synergistically effective amount of a cuprammonium compound and a triazole biocide.

U.S. Pat. No. 5,730,907 (U.S. '907) teaches the combination of an antioxidant with three organic biocides such as a quaternary ammonium compound, e.g., didecyldimethyl ammonium chloride (DDAC), an isothiazolone, or an isophthalonitrile gave an enhanced effect in protecting a hardwood against a white-rot fungus, Irpex lateus. The patent also provides a method for the use of such composition and compositions so treated.

For ecological and economic reasons, it is desirable to minimize the amount of biocide used to achieve a preservative effect. Accordingly, the addition of antioxidants in accord with the present invention should reduce the preservative retention levels required, and consequently, greatly improve the economics of both hardwood and softwood preservative systems, and thereby provide a more environmentally benign approach to the preservation of wood.

SUMMARY OF THE INVENTION

We have found the unexpected utility of adding antioxidants to selected commercial biocides to protect hardwoods and softwoods from fungal decomposition. Selected antioxidants significantly increase the activity and effectiveness of biocides to treat hardwoods and softwoods.

Accordingly, the present invention provides a wood preservative composition comprising (a) at least one biocide, i.e., an iodopropargyl compound or a triazole compound, and (b) at least one antioxidant. The composition is especially effective when the antioxidant is a hindered phenol derivative. In addition to being highly effective, the wood preservative composition is environmentally safe and inexpensive to apply.

None of the above biocides are taught by the U.S. '907 patent. The antioxidant and biocides combinations used in the present invention are effective against white-rot fungi, such as Trametes versicolor, to protect hardwoods, and brown-rot fungi, such as Gloeophyllum trabeum, to protect softwoods. Thus, the present invention greatly increases the utility of both hardwoods and softwoods in applications where the products are susceptible to biodeterioration. For example, to protect softwood lumber, which is used in residential construction and is susceptible to brown-rot fungi attacks.

The antioxidant alone, such as butylated hydroxy toluene (BHT), has no effectiveness against either of the above fungi. The combination of an antioxidant and the foregoing organic biocides give greater efficacy than either component alone with a variety of woods, such as the hardwoods sweetgum and aspen, and the softwood southern yellow pine. Thus, the combination of the antioxidants and biocides of the present invention is synergistic against fungi.

Of particular practical importance is the discovery that the low-cost antioxidant BHT, which is commonly used as a food additive, when combined with a biocide of the invention has an enhanced and synergistic biocidal effect with minimal environmental effects.

DETAILED DESCRIPTION

In one embodiment, the present invention provides a wood preservative composition comprising an effective amount of at least one biocide and an effective amount of at least one antioxidant; wherein the biocide is an iodopropargyl compound having the structure:

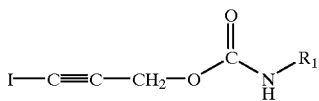

wherein $R_1$ is butyl, hexyl, cyclohexyl, or phenyl.

Preferably, $R_1$ is butyl (iodopropynylbutyl carbamate or IPBC).

In another embodiment, the present invention also provides a wood preservative composition comprising an effective amount of at least one biocide and an effective amount of at least one antioxidant; wherein the biocide is a triazole compound containing a triazole group having the structure:

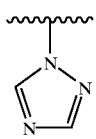

TRIAZOLE GROUP

Advantageously, the triazole compounds have the following formula:

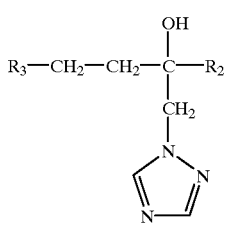

FORMULA A wherein $R_2$ is a branched or straight chain $C_{1-5}$ alkyl group (e.g., tert-butyl) and $R_3$ is an unsubstituted phenyl group or a substituted phenyl group having one or more substituents, i.e., halogen (e.g., chlorine, fluorine or bromine), $C_{1-3}$ alkyl (e.g., methyl), $C_{1-3}$ alkoxy (e.g., methoxy), phenyl, or nitro group.

Particularly preferred is a triazole compound of Formula A wherein $R_2$ is tert-butyl and $R_3$ is 4-chlorophenyl (alpha-[2-(4-chlorophenyl) ethyl] -alpha(1, 1 -dimethylethyl)-1H-1,2,4-triazole-1 -ethanol, commonly known as Tebuconazole).

Alternatively, the triazole compounds have the following formula:

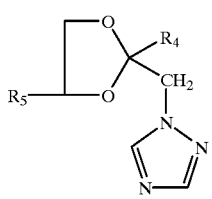

FORMULA B wherein $R_4$ is an unsubstituted phenyl group or a substituted phenyl group having one or more substituents, i.e., halogen (e.g., chlorine, fluorine or bromine), $C_{1-3}$ alkyl (e.g., methyl), $C_{1-3}$ alkoxy (e.g., methoxy), or nitro group; and $R_5$ is hydrogen or a branched or straight chain $C_{1-5}$ alkyl group (e.g., propyl).

Particularly preferred is a triazole compound of Formula B wherein $R_4$ is 2,4-dichlorophenyl and $R_5$ is propyl ((1-[[2-(2,4-dichlorophenyl)-4-propyl-1, 3-dioxolan-2-yl] methyl]-1H-1,2,4-triazole, commonly known as Propiconazole).

The antioxidants used in the present invention are hindered phenolics having the structure:

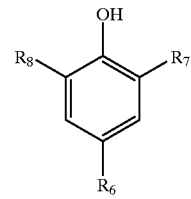

wherein $R_6$, $R_7$, and $R_8$ are the same or different and are selected from hydrogen, halogen, methoxy, a $C_{2-12}$ alkoxy, or a $C_{1-12}$ alkyl group.

The preferred hindered phenols used as antioxidants in the invention include the phenol shown above wherein $R_6$ is methoxy or methyl, and $R_7$ and $R_8$ are both tert-butyl (butylated hydroxy toluene (BHT) or butylated hydroxy anisole (BHA)); and the phenol wherein $R_6$ is hydrogen and $R_7$ and $R_8$ are both tert-butyl.

Other antioxidants which may be used include dimers, trimers, or tetramers of the hindered phenols having the basic structure above, such as tetrakis[methylene(3, 5-di-tert-butyl-4-hydroxy hydro-cinnamate)] or 4,4'-methylenebis (2,6-di-tert-butylphenol).

Another class of antioxidants which are useful in the present invention are polyphenols, which include flavonoids and other naturally occurring polyphenols.

The flavonoids have the following structure:

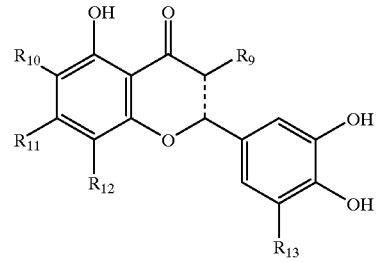

wherein $R_9$, $R_{10}$, $R_{11}$, $R_{12}$, and $R_{13}$ are the same or different and are hydrogen, hydroxyl, or a $C_{1-12}$ alkoxy group; and wherein the dashed line represents a single or a double bond.

The preferred flavonoid includes compounds wherein $R_9$ and $R_{11}$ are both hydroxyl and $R_{10}$, $R_{12}$, and $R_{13}$ are all hydrogen, and wherein the dashed line signifies a double bond (quercetin). Examples of the preferred flavonoids are chrysin, luteolin, myrcetin, hespertin and rhamnetin.

The naturally occurring polyphenols are those derived from woody plants. These antioxidants include, but are not limited to, tannins (or their isolated derivatives) and lignins (or their isolated derivatives), for example, kraft pulping lignin, lignin sulfonates, organosolve lignin, autohydrolysis lignin, acid-hydrolyzed lignin, and steam-exploded lignin. Tannins include quebracho, chestnuts, wattle, Pinus spp. bark condensed tannins, and the ellagitannins of chestnuts, oaks, and eucalyptus.

Examples of the preferred tannins and their derivatives are quebracho, wattle, Pinus spp. bark condensed tannins, chestnuts and oaks. Examples of the preferred lignins and their derivatives are kraft, lignin sulfonates and organosolve lignin.

The wood preservative composition disclosed herein may further comprise a liquid carrier medium such as a solvent and a suspending agent. Preferably the liquid carrier medium is a solvent such as water, ketones (e.g., acetone), alcohols (e.g. methanol, ethanol), esters (e.g. ethyl acetate), aromatic hydrocarbons (e.g. toluene), paraffinic hydrocarbons (e.g. hexanes and mineral spirits), or halogenated hydrocarbons (e.g. methylene chloride). The suspending agent may be a foam or gel. The composition may alternatively be applied as a solution in miscible mixtures of solvents or as an emulsion in multiphasic media by conventional means known in the art.

The composition of the invention may be provided not only as a diluted use solution but also as concentrates, emulsions, or suspensions of biocide.

The composition may also be formulated without added solvent or diluent as a powder or pellets.

If desired, conventional additives such as stabilizers, buffers, water-repellents, insecticides, pigments, odorants, coloring agents, surfactants, emulsifiers, flame-retardant compositions, and other additives may be added to the treating solution. The amount of such additives may vary over a range from about 0.01% to about 7% and preferably from about 0.01% to about 5% by weight.

The amount of the biocidal composition used in the composition and method of the invention is a "biocidal effective amount," i.e., an amount effective to inhibit the growth of, or kill, one or more organisms that cause wood rot Such organisms include but are not limited to, *Trametes versicolor* (*T versicolor*) and *Gloeophyllum trabeum* (*G. trabeum*). In the wood preservative composition of the invention, the weight ratio of the biocide to the antioxidant is from about 0.001:1 to about 3:1, preferably from about 0.05:1 to about 1:1 The biocide may be present in an amount of from about 0.01 to about 10% by weight and the antioxidant in an amount of from about 0.10 to about 12% by weight.

The wood is impregnated with the composition of the present invention by pressure-treating the wood with about 1 gallon of treating solution for each board-foot of lumber. About 20% to 50% of the solution is absorbed by the wood. Contact times of about 2 hours are typically used. Generally, 1,000 board feet of lumber requires about 1,000 gallons of treating solution which is administered during a contact period of between about 1 and about 6 hours.

In yet another embodiment, the present invention also provides a method for preserving wood against destructive fungi which comprises contacting wood with a biocidally effective concentration of the wood preservative composition as defined above in a carrier liquid. Accordingly, the method permits preserving wood against at least one of the above fungi.

Treatments of wood, e.g., lumber, timber, etc., can be carried out by conventional techniques including, but not limited to, dipping, spraying, brushing, pressure impregnation, and vacuum treatment. The length of the treatment time required will vary according to the treatment conditions, the selection of which is well known to those skilled in the art.

In yet another embodiment, the present invention also provides wood preserved against destructive fungi by the method which comprises contacting the wood with a biocidally effective concentration of the wood preservative composition as defined above.

Throughout this application, various references are cited within parentheses. These publications are hereby incorporated by reference to more fully describe the state of the art to which this invention pertains.

This invention will be better understood from the Examples which follow. However, one skilled in the art will readily appreciate that the specific methods and results discussed herein are merely illustrative of the invention as described more fully in the claims which follow thereafter. Unless otherwise indicated, all parts and percentages in the Examples and the present specification are by weight.

To show that free radical scavengers (primary antioxidants) will increase the efficacy of commercial biocides used as wood preservatives, two tests are performed: (1) agar-block test as shown in Example 1; and (2) soil-block test as shown in Example 2 These tests are defined in the Examples below.

The wood used in the agar- and soil-block tests includes aspen sapwood and southern yellow pine sapwood, respectively, selected according to AWPA standard E 10-91. The white-rot fungi examined was *Trametes versicolor* (ATCC# 12679) and the brown-rotter was *Gloeophyllum trabeum* (ATCC# 11539). Samples treated with the antioxidant alone, or biocide alone at four different retention levels, were tested and the degree of fungi attack were compared with samples treated with the combination of antioxidant and biocide at the same retention levels. Two sets of untreated samples were also tested in each experimental set as controls, i.e., control set and container control. Throughout this experiment, the term "treated samples" means samples exposed to either biocide alone or biocide mixed with antioxidants, as opposed to the term "untreated samples".

Each experimental set of a given retention level of biocide and/or antioxidant was performed with five replicate wood samples. These treated samples were placed into two cups, which contained the appropriate agar or soil, for incubation. Three samples were placed into one cup and the remaining two samples were placed into the second cup along with an untreated sample. The untreated sample placed into the second cup is called a "container control". Thus each set consists of five replicate treated samples of a given retention level of biocide and/or antioxidant and one additional untreated sample, which serves as a control. As a separate experiment, five untreated samples were placed into two cups as described above to provide the average strength loss data of the untreated samples. These five untreated samples are called the "control set".

The average retentions are reported in pounds of preservative per cubic foot of wood (pcf), as is normal in the wood preservative industry. The biocide effectiveness is determined by percent compression strength loss of the sample, as tabulated below. In certain cases, the average retentions represent the toxic threshold value of such biocide. "Threshold" is defined by the American Wood Preservers' Association Standards as the minimum amount of preservative that is effective in preventing significant wood decay, under the conditions of the test, by a particular fungus. This amount of preservative, expressed in $kg/m^3$ or pcf, is referred to as the "threshold retention". To establish the threshold value, the wood must be treated with a high enough concentration of biocide, to completely inhibit fungal degradation. As explained previously, the object of this experiment is not to increase the concentration of the biocide but to increase its efficiency. Thus, for the purposes of this experiment, only four different concentrations of the antioxidant/biocide combinations were run against both white-rot and brown-rot fungi, and as a result, the toxic threshold may not be reached. In these cases, the toxic threshold value of the preservative is higher than the tested highest concentration of the biocide without the antioxidant and appears to be lower than or equal to the tested lowest concentration of the biocide with the antioxidant. Even when the toxic threshold is not reached, the data set forth below show that the antioxidant/biocide combination at a given concentration is more effective than the biocide alone at the same concentration.

EXAMPLE 1

Agar Block Test

Wood sticks of aspen sapwood (Populus spp.) were cut into thin 10 block samples of 5 mm×19 mm×19 mm. These 10 samples were paired up into 5 matching-paired samples and treated with 5% of BHT alone (see Table I). Additional aspen samples were treated with one of the following biocides: Propiconazole (see Table IIa), Tebuconazole (see Table IIb), or IPBC (see Table III), with and without 5% added BHT antioxidant. The solvent used was toluene. In addition, two sets of untreated controls, labeled the container controls and the control set as described above, were also run. One sample of each of the five treated matching-paired samples were exposed to the white-rot fungus *T. versicolor* in the agar block test described by (Archer, K, et al., *For. Prod. J* 45(1) 86–89, (1995)). The incubation period was four weeks. The samples were then saturated with water to above their fiber saturation point before their degree of white rot attacks was determined. The degree of attack was determined by measuring the compression strength of each of the five samples exposed to the fungus relative to the compression strength of its matched and treated, but not fungus-exposed, paired sample. The biocide effectiveness is then determined and the results are reported in percent compression strength loss of the samples in the following tables.

The results for the antioxidant (5% BHT) alone in the agar-block test are shown in Table I below.

TABLE I

| Antioxidant/Average Retention (pcf) | Avg % Strength Loss ± Std. Dev. |
| --- | --- |
| BHT/1.507 | 176.85 ± 18.07 |
| Control Set | 87.97 ± 6.82 |
| Container Control | 95.58 ± 3.18 |

The data in Table I clearly show that the use of 5% BHT provides essentially no protection against fungal attack as compared to the untreated control samples, with all sets losing 70% or more strength.

The results for Propiconazole and Tebuconazole are shown in Tables II(a) and II(b) below, with and without an antioxidant. The symbol "***" signifies the approximate toxic threshold values, as defined above, for these biocides with and without an antioxidant. A definite toxic threshold value was not established for the Propiconazole/BHT combination, but the toxic threshold value appears to be less than or equal to 0.004 pcf.

TABLE II(a)

| Biocide/Avg Ret. (pcf); Antioxidant/Avg Ret. (pcf) | Avg % Strength Loss ± Std. Dev. | |
| --- | --- | --- |
| Propiconazole/0.049; None | 1.89 ± 4.36 | |
| Propiconazole/0.023; None | 1.38 ± 6.38 | *** |

TABLE II(a)-continued

| Biocide/Avg Ret. (pcf); Antioxidant/Avg Ret. (pcf) | Avg % Strength Loss ± Std. Dev. |
| --- | --- |
| Propiconazole/0.012; None | 42.40 ± 18.77 |
| Propiconazole/0.004; None | 89.95 ± 3.55 |
| Propiconazole/0.044; BHT/1.825 | 1.96 ± 3.05 |
| Propiconazole/0.022; BHT/1.855 | −1.37 ± 3.05 |
| Propiconazole/0.011; BHT/1.756 | 9.43 ± 16.63 |
| Propiconazole/0.004; BHT/1.830 | −2.73 ± 5.71 |
| Control Set | 97.04 ± 3.14 |
| Container Control | 75.10 ± 21.01 |

TABLE II(b)

| Biocide/Avg Ret. (pcf); Antioxidant/Avg Ret. (pcf) | Avg % Strength Loss ± Std. Dev. | |
| --- | --- | --- |
| Tebuconazole/0.047; None | 3.02 ± 4.69 | |
| Tebuconazole/0.023; None | 5.78 ± 15.38 | *** |
| Tebuconazole/0.012; None | 13.31 ± 11.33 | |
| Tebuconazole/0.004; None | 56.57 ± 15.97 | |
| Tebuconazole/0.046; BHT/1.927 | 1.62 ± 2.39 | |
| Tebuconazole/0.023; BHT/1.899 | 2.31 ± 1.81 | |
| Tebuconazole/0.011; BHT/1.867 | 5.05 ± 7.76 | *** |
| Tebuconazole/0.004; BHT/1.874 | 35.37 ± 47.37 | |
| Control Set | 97.04 ± 3.14 | |
| Container Control | 75.10 ± 21.01 | |

The data in Tables II(a) and II(b) clearly show that the addition of small amounts of BHT produced a substantial increase in the activity of both biocides (less strength loss). For example, adding as little as 1.867 pcf BHT reduced the toxic threshold values of Tebuconazole from about 0.023 pcf to about 0.011 pcf. Since BHT alone (see Table I) has no activity against wood strength loss and Tebuconazole alone was less active against wood strength loss than the combination of Tebuconazole and BHT, this shows that the combination of biocide and antioxidant is synergistic.

The results for IPBC are shown in Table III below, with and without an antioxidant. The symbol "***" signifies the toxic threshold values for IPBC in each set of runs with and without an antioxidant.

TABLE III

| Biocide/Avg Ret. (pcf); Antioxidant/Avg Ret. (pcf) | Avg % Strength Loss ± Std. Dev. | |
| --- | --- | --- |
| IPBC/0.052; None | 0.061 ± 1.82 | |
| IPBC/0.027; None | 3.062 ± 6.90 | *** |
| IPBC/0.012; None | 41.188 ± 33.30 | |
| IPBC/0.004; None | 77.696 ± 12.31 | |
| IPBC/0.051; BHT/1.973 | 3.060 ± 3.60 | |
| IPBC/0.027; BHT/1.922 | 0.503 ± 6.95 | |
| IPBC/0.012; BHT/1.936 | 2.086 ± 2.19 | *** |
| IPBC/0.004; BHT/1.886 | 40.12 ± 52.16 | |
| Control Set | 86.36 ± 1.98 | |
| Container Controls | 95.06 ± 4.76 | |

The data in Table III clearly show that the addition of small amounts of BHT produced a substantial increase in the activity of IPBC (less strength loss). For example, adding as little as 1.886 pcf BHT reduced the toxic threshold values of IPBC from about 0.027 pcf to about 0.012 pcf Since BHT alone (see Table I) has no activity against wood strength loss and IPBC alone has less activity against wood strength loss than the combination of IPBC and BHT, this again shows that the combination of biocide and antioxidant is clearly synergistic.

EXAMPLE 2

Soil Block Test

Wood sticks of southern yellow pine (Pinus spp.) sapwood blocks, cut in the same manner as described in Example 1, were treated with 5% of the antioxidant BHT alone (see Table IV). Additional southern yellow pine samples were treated with one of the following biocides: Propiconazole (see Table Va), Tebuconazole (see Table Vb), and IPBC (see Table VI), with and without 5% added BHT. In addition, two sets of untreated controls, labeled the container controls and the control set as described above were also run. One sample of each of the five treated matching-paired samples were exposed to the brown-rot fungus G. trabeum in the soil-block test described by (Archer, K., et al, *For. Prod J.* 45(1), 86–89, (1995)). The incubation period was four weeks. The samples were then saturated with water to above their fiber saturation point before the degree of brown rot degradation was determined. The degree of attack was determined as described in example 1.

The results for the antioxidant (5% BHT) alone in the soil-block test are shown in Table IV below.

TABLE IV

| Antioxidant/Average Retention (pcf) | Avg % Strength Loss ± Std. Dev. |
|---|---|
| 5% BHT/1.597 | 93.27 ± 1.35 |
| Untreated Control | 96.53 ± 0.65 |
| Container Controls | 96.25 ± 0.90 |

The data in Table IV clearly show that the use of 5% BHT provides essentially no protection against fungal attack as compared to the untreated control samples, with all sets losing 90% or more strength.

The results for Propiconazole and Tebuconazole are shown in Tables V(a) and V(b) below, respectively, with and without an antioxidant. The Tebuconazole samples were incubated for a total of 47 days because of limited fungicidal degradation at 25 days. No toxic threshold values for Propiconazole were established with or without BHT, which signifies that the toxic threshold value for Propiconazole is greater than 0.044 pcf.

TABLE V(a)

| Biocide/Avg Ret. (pcf); Antioxidant/Avg Ret. (pcf) | Avg % Strength Loss ± Std. Dev. |
|---|---|
| Propiconazole/0.042; None | 30.82 ± 6.67 |
| Propiconazole/0.021; None | 69.90 ± 16.80 |
| Propiconazole/0.011; None | 93.92 ± 1.50 |
| Propiconazole/0.004; None | 95.53 ± 0.77 |
| Propiconazole/0.044; BHT/1.82 | 12.69 ± 5.14 |
| Propiconazole/0.021; BHT/1.78 | 30.55 ± 6.18 |
| Propiconazole/0.011; BHT/1.82 | 41.14 ± 2.81 |
| Propiconazole/0.004; BHT/1.79 | 39.10 ± 2.23 |
| Control Set | 96.67 ± 0.50 |
| Container Control | 98.35 ± 2.12 |

TABLE V(b)

| Biocide/Avg Ret. (pcf); Antioxidant/Avg Ret. (pcf) | Avg % Strength Loss ± Std. Dev. | |
|---|---|---|
| Tebuconazole/0.038; None | 5.99 ± 2.45 | |
| Tebuconazole/0.020; None | 1.42 ± 8.92 | *** |
| Tebuconazole/0.010; None | 19.21 ± 15.78 | |
| Tebuconazole/0.003; None | 84.64 ± 9.61 | |
| Tebuconazole/0.040; BHT/1.70 | −12.67 ± 28.40 | |
| Tebuconazole/0.020; BHT/1.67 | −3.47 ± 3.37 | |
| Tebuconazole/0.010; BHT/1.64 | 2.07 ± 10.64 | |
| Tebuconazole/0.003; BHT/1.62 | −0.98 ± 4.36 | *** |
| Control Set | 97.08 ± 0.07 | |
| Container Control | 96.65 ± 6.95 | |

The data in Tables V(a) and V(b) clearly show that the addition of small amounts of BHT produced a substantial increase in the activity of both biocides (less strength loss). For example, adding as little as 1.6 pcf BHT reduced the toxic threshold values of Tebuconazole from about 0.020 pcf to less than or equal to 0.003 pcf. Since BHT alone (see Table I) has no activity against wood strength loss and Tebuconazole alone has less activity against wood strength loss than the combination of Tebuconazole and BHT, this clearly shows that the combination of biocide and antioxidant is synergistic.

The results for IPBC are shown in Table VI below, with and without an antioxidant. The symbol "***" signifies the toxic threshold values for IPBC with and without an antioxidant. A toxic threshold value was not established for IPBC alone, which signifies that without BHT, the toxic threshold value of IPBC is greater than 0.045 pcf.

TABLE VI

| Biocide/Avg Ret. (pcf); Antioxidant/Avg Ret. (pcf) | Avg % Strength Loss ± Std. Dev. | |
|---|---|---|
| IPBC/0.045; None | 48.708 ± 31.26 | |
| IPBC/0.024; None | 56.347 ± 19.62 | |
| IPBC/0.010; None | 66.841 ± 21.23 | |
| IPBC/0.003; None | 74.919 ± 31.75 | |
| IPBC/0.044; BHT/1.689 | 4.991 ± 5.94 | *** |
| IPBC/0.023; BHT/1.611 | 8.435 ± 4.17 | |
| IPBC/0.010; BHT/1.712 | 68.592 ± 24.38 | |
| IPBC/0.003; BHT/1.662 | 87.68 ± 3.26 | |
| Untreated Control | 91.56 ± 18.87 | |
| Container Controls | 87.20 ± 19.67 | |

The data in Table VI clearly show that the addition of small amounts of BHT produced a substantial increase in the activity of IPBC (less strength loss). For example, adding as little as 1.611 pcf BHT reduced the toxic threshold values of IPBC from greater than 0.045 pcf to about 0.044 pcf. Since BHT alone (see Table I) has no activity against wood strength loss and IPBC alone has less activity against wood strength loss than the combination of IPBC and BHT, this clearly shows that the combination of biocide and antioxidant is synergistic.

Discussion

These experiments show that the activity of low concentrations of biocides used as hardwood and softwood preservatives can be significantly increased by adding antioxidants by the methods disclosed herein. Specifically, the addition of an antioxidant to biocides results in a significantly more active wood preservative.

Variations of the present invention will suggest themselves to those skilled in the art, and are within the scope of the following claims.

We claim:

1. A wood preservative composition comprising:
   (a) a biocidal effective amount of at least one biocide selected from the group consisting of:

(i) an iodopropargyl compound having the structure:

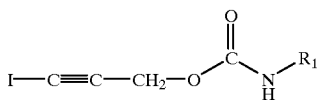

wherein $R_1$ is butyl, hexyl, cyclohexyl, or phenyl; or
(ii) a triazole compound of Formula A:

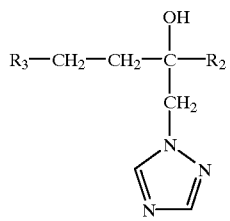

wherein $R_2$ is a branched or a straight chain $C_{1-5}$ alkyl group; $R_3$ is an unsubstituted phenyl or a substituted phenyl group having one or more substituents selected from the group consisting of halogen, $C_{1-3}$ alkyl, $C_{1-3}$ alkoxy, and nitro group; or
(iii) a triazole compound of Formula B

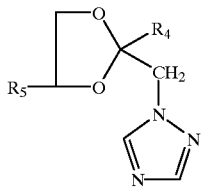

wherein $R_4$ is an unsubstituted phenyl or a substituted phenyl group having one or more substituents selected from the group consisting of halogen, $C_{1-3}$ alkyl, $C_{1-3}$ alkoxy, and nitro group; and $R_5$ is a hydrogen atom or a branched or a straight chain $C_{1-5}$ alkyl group; and
(b) an amount of at least one antioxidant sufficient to increase the efficacy of the biocide, wherein the antioxidant is:
(i) a hindered phenol having the formula:

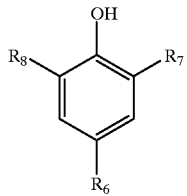

wherein $R_6$, $R_7$, and $R_8$ are the same or different and are selected from the group consisting of hydrogen, halogen, methoxy, $C_{2-12}$ alkoxy, and $C_{1-12}$ alkyl group; or
(ii) a naturally occurring polyphenolic compound found in woody plants.

2. The wood preservative composition of claim 1 wherein the naturally occurring polyphenolic compound is tannin, lignin or a naturally occurring derivative thereof.

3. The wood preservative composition of claim 1 wherein the biocide is the iodopropargyl compound wherein $R_1$ is butyl.

4. The wood preservative composition of claim 3 wherein the antioxidant is the hindered phenol wherein $R_6$ is methyl and $R_7$ and $R_8$ are tert-butyl.

5. The wood preservative composition of claim 1 wherein the biocide is the triazole compound of Formula A wherein $R_2$ is tert-butyl and $R_3$ is 4-chlorophenyl.

6. The wood preservative composition of claim 5 wherein the antioxidant is the hindered phenol wherein $R_6$ is methyl and $R_7$ and $R_8$ are tert-butyl.

7. The wood preservative composition of claim 1 wherein the biocide is the triazole compound of Formula B wherein $R_4$ is 2,4-dichlorophenyl and $R_5$ is propyl.

8. The wood preservative composition of claim 7 wherein the antioxidant is the hindered phenol wherein $R_6$ is methyl and $R_7$ and $R_8$ are tert-butyl.

9. The wood preservative composition of claim 1 further comprising a liquid carrier medium selected from the group consisting of a solvent and suspending agent.

10. The wood preservative composition of claim 9 wherein the liquid carrier medium is selected from the group consisting of alcohols, ketones, water, esters, aromatic hydrocarbons, paraffinic hydrocarbons, and halogenated hydrocarbons.

11. The wood preservative composition of claim 1 wherein the weight ratio of the biocide to the antioxidant is from about 0.001:1 to about 3:1.

12. The wood preservative composition of claim 11 wherein the weight ratio is from about 0.05:1 to about 1:1.

13. The wood preservative composition of claim 1 wherein the biocide is present in an amount of from about 0.01 to about 10% by weight and the antioxidant is present in an amount of from about 0.10 to about 12% by weight, based upon 100% total weight of wood preservative composition.

14. The wood preservative composition of claim 13 wherein the biocide is the iodopropargyl compound wherein $R_1$ is butyl; the triazole compound of Formula A wherein $R_2$ is tert-butyl and $R_3$ is 4-chlorophenyl; or the triazole compound of Formula B wherein $R_4$ is 2,4-dichlorophenyl and $R_5$ is propyl.

15. The wood preservative composition of claim 13 wherein the antioxidant is the hindered phenol wherein $R_6$ is methyl and $R_7$ and $R_8$ are tert-butyl.

16. The wood preservative composition of claim 1, wherein the biocide is iodopropynylbutyl carbamate and the antioxidant is butylated hydroxy toluene.

17. The wood preservative composition of claim 1, wherein the biocide is iodopropynylbutyl carbamate and the antioxidant is tannin.

18. The wood preservative composition of claim 1, wherein the biocide is tebuconazole and the antioxidant is butylated hydroxy toluene.

19. The wood preservative composition of claim 1, wherein the biocide is tebuconazole and the antioxidant is tannin.

20. The wood preservative composition of claim 1, wherein the biocide is propiconazole and the antioxidant is butylated hydroxy toluene.

21. The wood preservative composition of claim 1, wherein the biocide is propiconazole and the antioxidant is tannin.

22. A method of preserving wood which comprises impregnating wood with the wood preservative composition of claim 1.

23. The method of claim 22, wherein the biocide is iodopropynylbutyl carbamate and the antioxidant is butylated hydroxy toluene.

24. The method of claim 22, wherein the biocide is iodopropynylbutyl carbamate and the antioxidant is tannin.

25. The method of claim 22, wherein the biocide is tebuconazole and the antioxidant is butylated hydroxy toluene.

26. The method of claim 22, wherein the biocide is tebuconazole and the antioxidant is tannin.

27. The method of claim 22, wherein the biocide is propiconazole and the antioxidant is butylated hydroxy toluene.

28. The method of claim 22, wherein the biocide is propiconazole and the antioxidant is tannin.

29. A method of preserving wood which comprises impregnating wood with the wood preservative composition of claim 13.

30. The method of preserving wood of claim 29 wherein the antioxidant is the hindered phenol wherein $R_6$ is methyl and $R_7$ and $R_8$ are tert-butyl.

31. The method of preserving wood of claim 29 wherein the biocide is the iodopropargyl compound wherein $R_1$ is butyl; the triazole compound of Formula A wherein $R_2$ is tert-butyl and $R_3$ is 4-chlorophenyl; or the triazole compound of Formula B wherein $R_4$ is 2,4-dichlorophenyl and $R_5$ is propyl.

32. Wood preserved by the method of claim 22.

33. Wood preserved by the method of claim 29.

* * * * *